United States Patent [19]

Bahary et al.

[11] Patent Number: 5,658,574
[45] Date of Patent: Aug. 19, 1997

[54] CLEANSING COMPOSITIONS WITH DENDRIMERS AS MILDNESS AGENTS

[75] Inventors: William Shaul Bahary, Pearl River, N.Y.; Michael Patrick Hogan, Rochelle Park, N.J.

[73] Assignee: Chesebrough-Pond's USA Co., Division of Conopco, Inc., Greenwich, Conn.

[21] Appl. No.: 542,750

[22] Filed: Oct. 13, 1995

[51] Int. Cl.$^6$ ..................................................... A61K 9/00
[52] U.S. Cl. .................................. 424/400; 424/DIG. 16
[58] Field of Search ........................... 424/400, DIG. 16

[56] References Cited

U.S. PATENT DOCUMENTS

| | | | |
|---|---|---|---|
| 4,438,095 | 3/1984 | Grollier et al. | 424/70 |
| 4,673,525 | 6/1987 | Small et al. | 252/132 |
| 4,713,236 | 12/1987 | Hoover et al. | 424/70 |
| 4,812,253 | 3/1989 | Small et al. | 252/132 |
| 4,820,447 | 4/1989 | Medcalf et al. | 252/117 |
| 4,946,618 | 8/1990 | Knochel et al. | 252/117 |
| 4,985,170 | 1/1991 | Dawson et al. | 252/132 |
| 5,296,159 | 3/1994 | Wilson et al. | 252/117 |
| 5,322,643 | 6/1994 | Schwartz et al. | 252/554 |
| 5,338,532 | 8/1994 | Tomalia et al. | 424/1.49 |
| 5,496,555 | 3/1996 | Colwell | 424/405 |
| 5,560,929 | 10/1996 | Hedstrand et al. | 424/486 |

FOREIGN PATENT DOCUMENTS

| | | |
|---|---|---|
| 0 308 189 | 3/1989 | European Pat. Off. . |
| 0 308 190 | 3/1989 | European Pat. Off. . |
| WO 88/01178 | 2/1988 | WIPO . |

OTHER PUBLICATIONS

Dendritech Product Brochure, 1995 The Dow Chemical Company.

Tomalia, D. et al., *Angew. Chem. Int. Ed. Engl.*, vol. 29, (1990), pp. 138–175.

Tomalia, D., *Aldrichimica Acta.*, vol. 26, No. 4, (1993), pp. 91–101.

Tomalia, D. et al., "Dendritic Polymers" in *Encycl. Polym. Sci. & Eng.*, Index vol., 2nd ed., Wiley, 1990, pp. 46–92.

Abstract of WO 94/03151.

O'Sullivan, D., "Dendrimers Nearing Availability for Commercial Evaluation", Chem & Eng News, Aug. 16, 1993, pp. 20–23.

*Primary Examiner*—Joseph L. Schofer
*Assistant Examiner*—Wu C. Cheng
*Attorney, Agent, or Firm*—Rimma Mitelman

[57] ABSTRACT

Personal wash compositions containing an anionic surfactant as a cleaning agent and a cationic dendrimer as a mildness aid. The dendrimer lowers the irritation potential of the surfactant. Cationic dendrimers remain dispersed in anionic surfactant solutions. The dendrimers are significantly less viscous than linear cationic polymeric mildness aids and are monodispersed. Furthermore, the dendrimers perform better than linear cationic polymers, especially in the presence of harsh anionic surfactants such as sodium dodecyl sulfate.

11 Claims, No Drawings

CLEANSING COMPOSITIONS WITH DENDRIMERS AS MILDNESS AGENTS

FIELD OF THE INVENTION

The invention relates to personal wash compositions containing an anionic surfactant. The compositions contain specific dendrimers as mildness agents to ameliorate the harsh effects of the anionic surfactant.

BACKGROUND OF THE INVENTION

Dendrimers are polymers. Dendrimers may be cationic (full generation dendrimers) or anionic (half generation dendrimers). Dendrimers are also known as "starburst" or "star" polymers, due to a characteristic star-like structure. Tomalia reviewed the synthesis, physical properties, and applications of dendrimers. See, e.g., Tomalia et. al, *Angew. Chem. Int. Ed. Engl.*, 29, 138–175, (1990); Tomalia, *Aldrichimica Acta*, 26, No. 4, pp. 91–101 (1993); Tomalia et al., "Dendritic Polymers" in *Encycl. Polym. Sci. & Eng.*, Index Vol., 2nd ed., Wiley, 1990, pp. 46–92. No mention is made of personal washing compositions containing dendrimers or dendrimers' use as mildness agents.

PCT application WO 88/01178 (Tomalia et al., assigned to the Dow Chemical Company) describes starburst conjugates which are composed of a dendrimer in association with a pharmaceutical material. Dendrimers are employed for targeted delivery of active molecules. Examples of the pharmaceutical materials are drugs or scavenging agents. U.S. Pat. No. 5,338,532 (Tomalia et al.) contains a similar disclosure of dendrimer/active conjugates. The disclosed applications include drug delivery, targeted delivery, complexation with metals for contrast imaging, and complexation with fragrances and dyes for controlled delivery.

A wide variety of personal wash compositions is available to a consumer. Consumers prefer milder (less harsh to the skin) cleansers. Unfortunately, best lathering is obtained from soap or synthetic surfactants which typically do not perform well in clinical mildness tests.

One method of providing skin benefits (e.g., mildness) is through the use of polymeric mildness aids. Cationic polymers, other than dendrimers, have previously been employed as mildness agents in soap bars and liquid cleansing formulations. For instance, U.S. Pat. No. 5,296,159 (Wilson et al.) discloses mild soap bars containing a cationic polymer, such as cationic polysaccharides, cationic copolymers of saccharides and synthetic cationic monomers, and cationic synthetic polymers. Examples of the latter are polyalkylene imine (e.g., polyethylene imine), ethoxy polyalkylene imine, and cationic polyionene (e.g., Mirapol A-15 from Miranol Chem. Co.). U.S. Pat. No. 4,713,236 (Hoover et al.) discloses polymers containing primary pendant amine groups (e.g., polyvinylamine) for imparting good conditioning properties to hair.

Personal wash compositions containing cationic polymeric mildness aids are also disclosed in U.S. Pat. No. 5,322,643 (Schwartz et al.), U.S. Pat. No. 4,820,447 (Medcalf et al.), U.S. Pat. No. 4,985,170 (Dawson et al.), U.S. Pat. No. 4,946,618 (Knochel et al.), U.S. Pat. No. 4,438,095 (Grollier et al, U.S. Pat. No. 4,812,253 (Small et al.), U.S. Pat. No. 4,673,525 (Small et al.), European Patent Application 0 308 190 (Procter & Gamble), European Patent Application No. 0 308 189 (Procter & Gamble), and PCT Application WO 94/03151 (Unilever).

Unfortunately, cationic mildness aids often co-precipitate with anionic surfactants which detracts from the performance of both the anionic surfactant and the cationic polymer, which in turn results in decreased lathering, cleaning, and skin conditioning. A further drawback is that cationic mildness aids are polymers and therefore are quite viscous which in turn presents difficulties in processing the formulations and achieving a uniform distribution of a mildness aid in the final formulation. Also, cationic polymeric aids typically have a broad molecular weight distribution—this makes the formulation of a cleanser more difficult because the polymer will not necessarily function as a mildness aid over the entire molecular weight range. Thus, a continuous need exists to improve personal washing compositions to deliver optimum mildness, cleaning, and processing ease.

Accordingly, it is an object of the present invention to provide a mild personal washing composition while avoiding the disadvantages of the prior art.

It is another object of the invention to provide personal washing compositions containing specific dendrimers as mildness agents.

It is still another object of the invention to provide a method of cleaning the skin while avoiding the harsh effects on the skin of an anionic surfactant or by washing the skin with the inventive composition.

These and other objects of the invention will become more apparent from the detailed description and examples that follow.

SUMMARY OF THE INVENTION

The above objects are attained by the present invention which includes, in part, a mild personal cleansing composition containing from about 0.05 to about 40 wt. % of a cationic dendrimer of generation n, wherein n is an integer from 0 to 10, and from about 1% to about 99% of an anionic surfactant.

The structure and properties of dendrimers differ from the structure and properties of their linear counterparts. Dendrimers have a unique star-like branched architecture.

The present invention is based in part on a discovery that certain cationic dendrimers decrease skin irritation potential of anionic surfactants to the same or to a greater extent compared to their linear counterparts, while dendrimers remain dispersed in anionic surfactant solutions. By contrast, linear cationic polymers employed in the prior art co-precipitate with an anionic surfactant and do not redisperse. Another advantage of dendrimers is their low viscosity, even for dendrimers with a relatively high molecular weight. Dendrimers have significantly lower viscosities compared to linear cationic polymers. See Table IA below. Furthermore, dendrimers have a narrow molecular weight distribution. For example, polyvinylamine (the closest linear counterpart to a polyamidoamine dendrimer) has a broad molecular weight distribution with a polydispersity of 2.5 whereas polyamidoamine dendrimers are essentially monodispersed (i.e., polydispersity of about 1.0). Polydispersity is defined as the ratio of weight average to number average molecular weight.

While not wishing to be bound by this theory, it is believed that a linear cationic polymer maintains a random coil configuration in salt solutions and readily forms a precipitate with anionic surfactants. However, dendrimers can bind surfactants in a cooperative manner, and remain dispersed more easily.

The inventive composition may be in the form of bar soaps, or gels, (i.e., a shower gel), or liquids.

The invention also includes a method of cleaning and conditioning the skin while avoiding the harsh effects on the skin of an anionic surfactant by washing the skin with the inventive composition.

DESCRIPTION OF THE PREFERRED EMBODIMENT

The inventive compositions contain, as a first essential ingredient, a cationic dendrimer. The dendrimers are a new class of hyperbranched molecules with specific architecture and molecular weight. The term "cationic" as used herein includes amine-terminated dendrimers and quaternized forms thereof. The term "amine-terminated" includes primary, secondary and tertiary amines.

Examples of the dendrimers include but are not limited to polyamidoamines (hereinafter "PAMAM") or polyethyleneimine or polypropylene imine. The preferred dendrimers are polyamidoamine dendrimers because they are more biogradable/biocompatible (polyamidoamine groups resemble peptide bonds of proteins). The polyamidoamine dendrimers are prepared by sequential reactions of ethylenediamine and methyl acrylate as shown below:

Polyamidoamine dendrimers may be prepared having different molecular weights and have specific values as described in Table A below for generations 0 through 10.

TABLE A

LIST OF PAMAM DENDRIMERS AND THEIR MOLECULAR WEIGHTS Ethylene Diamine CORE, AMINE-TERMINATED

| GENERATION | # TERMINAL GROUPS | MOL. WT. g/mole |
|---|---|---|
| 0 | 4 | 517 |
| 1 | 8 | 1430 |
| 2 | 16 | 3256 |
| 3 | 32 | 6909 |
| 4 | 64 | 14,215 |
| 5 | 128 | 28,795 |
| 6 | 256 | 58,048 |
| 7 | 512 | 116,493 |
| 8 | 1024 | 233,383 |
| 9 | 2048 | 467,162 |
| 10 | 4096 | 934,720 |

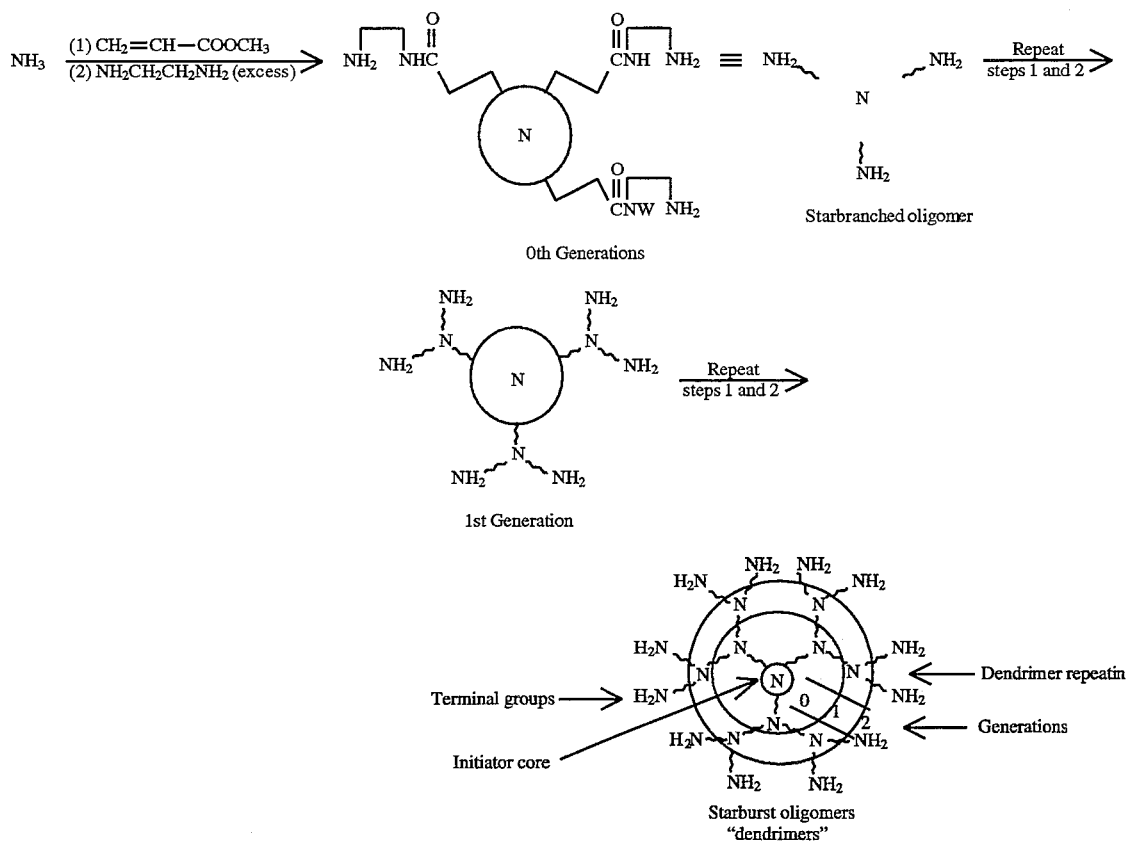

Dendrimers are prepared in tiers called generations and therefore have specific molecular weights. The full generation polyamidoamine dendrimers have amine terminal groups, whereas the half generations are carboxyl terminated.

Full generation polyamidoamine dendrimers are cationic and are within the scope of the present invention.

As shown in Table A, the number of terminal amine groups for polyamidoamine dendrimers generations 0 through 10 range from 4 to 4,096, with molecular weights of from 517 to 934,720. Polyamidoamine dendrimers are available commercially from Aldrich or Dendritech. Polyethyleneimine or polypropylene dendrimers or quaternized forms of amine-terminated dendrimers may be prepared as described by Tomalia et. al. *Angew, Chem. Int. Ed. Engl.*, 29, 138–175, (1990).

The preferred polyamidoamine dendrimers are those of generations 0 through 5, due to lower cost and ease of manufacture. Most preferably, the polyamidoamine dendrimers of generations 0 through 2 are employed to achieve mildness at optimum cost. The amine-terminated dendrimers are employed in the inventive compositions to provide mildness and decreased irritancy to cleansing materials.

A second essential ingredient of the inventive compositions is an anionic surfactant.

The anionic surfactant which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glycerol ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glycerol ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$ to $C_{22}$ sulfosuccinates); alkyl and acyl taurates, alkyl and acyl sarcosinates, sulfoacetates, $C_8$ to $C_2$ alkyl phosphates, alkyl phosphate esters and alkoxyl alkyl phosphate esters, acyl lactates, $C_8$ to $C_{22}$ monoalkyl succinates and maleates, sulphoacetates, alkyl glucosides and acyl isethionates.

Sulfosuccinates may be a monoalkyl sulfosuccinates having the formula:

$$R^4O_2CCH_2CH(SO_3M)CO_2M;\ and$$

amide-monoethanolamine sulfosuccinates of the formula $$R^4CONHCH_2CH_2O_2CCH_2CH(SO_3M)CO_2M$$

wherein $R^4$ ranges from $C_8$ to $C_{20}$ alkyl and M is a solubilizing cation.

Sarcosinates are generally indicated by the formula R'CON($CH_3$)$CH_2CO_2M$, wherein R ranges from $C_8$–$C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R_3$ ranges from $C_1$–$C_4$ alkyl and M is a solubilizing cation.

Particularly preferred anionics are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate may be an alkoxylated isethionate such as is described in Ilardi et al., U.S. application Ser. No. 07/796,748, now abandoned, hereby incorporated by reference. This compound has the general formula:

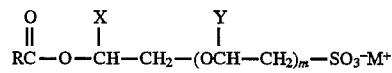

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

The cationic dendrimer is employed in the inventive compositions in an amount of from 0.05% to 40%. The amount of the anionic surfactant is in the range of from 1% to 99%. The precise amounts are determined by the form of the composition, i.e., liquid/gel or bar soap. General, preferred and most preferred ranges for bars and liquids are listed in Table B.

TABLE B

| | BARS | | LIQUIDS | |
|---|---|---|---|---|
| | Min. | Max. | Min. | Max. |
| | Dendrimers | | | |
| Broad | 0.5 | 40 | 0.05 | 25 |
| Preferred | 1 | 30 | 0.1 | 10 |
| Most preferred | 2 | 20 | 0.2 | 5 |
| | Anionic Surfactants | | | |
| Broad | 10 | 99 | 1 | 50 |
| Preferred | 25 | 85 | 3 | 40 |
| Most Preferred | 35 | 75 | 5 | 30 |

An additional surfactant may optionally be included in the inventive compositions. It may be any of the anionic surfactants discussed above except that it should be different than the first anionic component. The second surfactant may also be any of the amphoteric or nonionics discussed below as well as a mixture of the anionic, amphoteric and/or nonionic.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula.

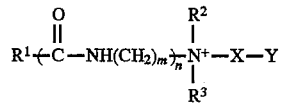

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

m is 2 to 4;

n is 0 to 1;

X is alkylene of 1 to 3 carbon atoms optionally substituted with hydroxyl, and

Y is —$CO_2^-$ or —$SO_3^-$

Suitable amphoteric detergents within the above general formula include simple betaines of formula:

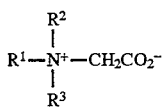

and amido betaines of formula:

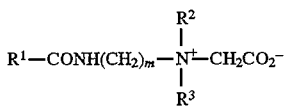

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

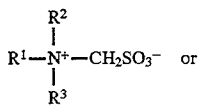

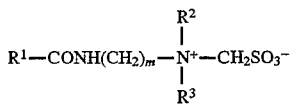

where m is 2 or 3, or variants of these in which —$(CH_2)_3SO_3^-$ is replaced by

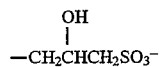

In these formulae $R^1$, $R^2$ and $R^3$ are as discussed previously.

The nonionic which may be used as the second component of the surfactant system include in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Ser. No. 816,419 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. which is also incorporated into the subject application by reference.

In general the second optional surfactant (i.e., second anionic, nonionic and/or amphoteric compound or mixture) is incorporated into the composition as less than 50% by weight, preferably 1 to 20% by weight of the composition.

Other Components

In addition, other optional components which may be included are as follows:

Skin mildness improvers also preferably used in the composition of the invention are salts of isethionate. Effective salts cations may be selected from the group consisting of alkali metal, alkaline earth metal, ammonium, alkyl ammonium and mono-, di- or tri-alkanolammonium ions. Specifically preferred cations include sodium, potassium, lithium, calcium, magnesium, ammonium, triethylammonium, monoethanolammonium, diethanolammonium or triethanolammonium ions.

Particularly preferred as a mildness improver is simple, unsubstituted sodium isethionate of the general formula $$HOCH_2CH_2SO^-_3M$$

The skin mildness improver will be present from about 0.1% to about 50%. Preferably, the mildness improver is present from about 0.5% to about 25%, more preferably from about 0.5% to about 10%, by weight of the total composition.

Other performance chemicals and adjuncts may be needed with these compositions. The amount of these chemicals and adjuncts may range from about 1% to about 40% by weight of the total composition. For instance, from 2 to 10% of a suds-boosting detergent salt may be incorporated. Illustrative of this type additive are salts selected from the group consisting of alkali metal and organic amine higher aliphatic fatty alcohol sulfates, alkyl aryl sulfonates, and the higher aliphatic fatty acid taurinates.

Adjunct materials including germicides, perfumes, colorants, pigments such as titanium dioxide and water may also be present.

Preferably, the pH of the compositions is not greater than about 8, preferably it is in the range of from 5 to 8, in order to maximize the mildness benefit.

The following specific examples further illustrate the invention, but the invention is not limited thereto.

All percentages in the specification and examples are intended to be by weight unless stated otherwise.

EXAMPLES

Description of Mildness Test

The novel polycations disclosed are tested for skin mildness by the modified zein solubilization test as described by Foster, J. F., *J. Phys. Colloid Chem.*, Vol. 53, pp. 175 (1949) and by Gotte, E., *Proc. Int. Cong. Surface Active Subs.*, 4th, Brussels, Vol. 3, pp. 83–90 (1964). Zein is a protein obtained from the hull substance of maize, and the percent solubilized by surfactants was shown to relate to the irritation potential of the surfactant in Diagrams 1 and 2 of Gotte. The more efficacious polycations reduce the amount of dissolved zein significantly in proportion to their mildness benefit.

Procedure

The test compositions were prepared as follows: In a 50 mL centrifuge tube, 30 mL of a 1% surfactant solution were added. Various tested mildness agents were added at various concentrations as indicated in the Examples below. The pH was adjusted to the desired level with HCl or NaOH. Then 1.5 g zein was added, stirred briefly, and placed on a shaker for one (1) hour. The tubes were centrifuged for 30 min. at approximately 3000 RPM. The undissolved zein was isolated, rinsed, and allowed to dry in a vacuum oven at 60° C. to constant weight. The percent zein solubilized, which is related to the irritation potential, is determined gravimetrically.

In the experiments that follow, the various actives were tested by the zein dissolution method using different surfactants systems.

Examples 1–33 demonstrate advantages of dendrimers over other cationic polymers.

EXAMPLES 1–10

In Examples 1–10, five polyamidoamine dendrimers of various molecular weights (generations 0–5) were tested for skin irritation potential in the presence of 1% sodium lauroyl isethionate (SLI) at pH=5.6. Three linear cationic polymers were tested (also in the presence of 1% SLI and at pH=5.6) in comparative Examples 6–8. Dendrimers or other polymers were included at 0.2%. Example 9 was a control sample with SLI but without any polymer, and Example 10 was plain water without any active or any surfactant. In several instances, a precipitate formed upon the addition of a tested mildness agent to the surfactant solution. The maximum precipitate weight that could theoretically be formed is 0.36 g. In a separate experiment, the precipitate was collected by centrifugation, dried and the weight determined. The weight of the unsolubilized zein pellet was corrected for the amount of SLI/polymer agent precipitate.

The results that were obtained are summarized in Table I.

TABLE I

| Example No. | Polymer | Wt. Precipitate SLI/Polymer | Corrected % Zein Solubilized |
|---|---|---|---|
| 1 | Gen 0* | 0.15 | 1.5 ± 0.62 |
| 2 | Gen 1* | 0.05 | 3.4 ± 0.41 |
| 3 | Gen 2* | 0.02 | 13.0 ± 1.26 |
| 4 | Gen 3* | 0.01 | 12.1 ± 0.21 |
| 5 | Gen 5* | 0.00 | 14.6 ± 0.50 |
| 6 | Mirapol A-15 | 0.00 | 16.8 ± 0.29 |
| 7 | Polyvinylamine | 0.12 | 5.3 ± 0.82 |
| 8 | Polyethyleneimine | 0.31 | 8.6 ± 0.05 |
| 9 | Control - SLI only | 0.00 | 47.0 ± 0.10 |
| 10 | Water | — | 10.4 ± 0.56 |

*polyamidoamine (PAMAM) dendrimers of generations 0 through 5

Polyvinylamine (example 7) is the linear counterpart of the dendrimers and has comparable molecular weight to Generation 5 polyamidoamine dendrimer. Polyethyleneimine (example 8) is a linear counterpart to the secondary amines of dendrimers. Mirapol A-15 is a quaternized ionene. The structures of compounds tested in Examples 6–8 are given below for ease of comparison with dendrimers.

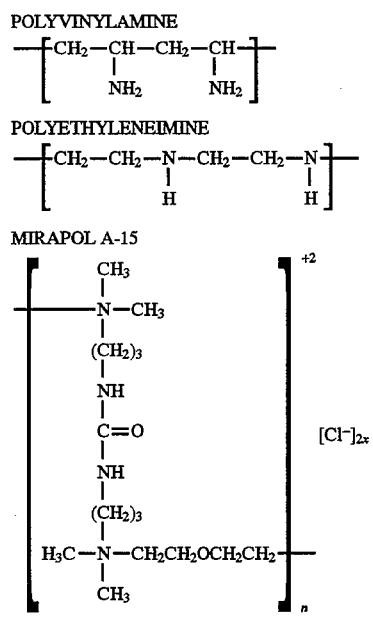

Polyethyleneimine and polyvinylamine are the closest linear counterparts to polyamidoamine dendrimers.

As can be seen from the results in Table I, the addition of either dendrimers or the cationic polymers of Examples 6–8, to the surfactant-containing solution substantially reduced the irritation potential compared to control. Generations 1 through 5 dendrimers yielded essentially no precipitate. This is surprising because the molecular weight of Generation 5 is similar to those of the polyethyleneimine and polyvinylamine. It is also unexpected that the dendrimers exhibit very low zein solubility, even though they do not precipitate the surfactant. On the other hand, although polyethyleneimine had a relatively low zein solubility, it precipitated with SLI, so that the resulting medium was essentially like water—no benefit could be expected from either SLI or polyethyleneimine. Indeed, % zein solubilized was comparable to that of water (about 10%). Mirapol A-15 appeared to perform as well as Generation 5 dendrimer with regard to zein solubility and low coprecipitation with anionic. But, as demonstrated in Examples 16–20 and 21 in Table III, in the presence of an anionic surfactant which is harsher than SLI, dendrimers lowered zein solubility to a substantially greater extent than Mirapol A-15.

The molecular weights and viscosities of various dendrimers and polymers of Examples 6–8 are summarized in Table IA below.

TABLE IA

|  | Gen 0 | Gen 2 | Gen 5 | PEI | PVam | Mirapol |
|---|---|---|---|---|---|---|
| Molecular Weight | 517 | 3,256 | 28,800 | 70,000 | 45,800 | 4,500 |
| Intrinsic Viscosity (dL/g) |  | 0.04 | 0.05 | 0.8 | 0.44 | 0.2 |

It can be seen from Table IA that PAMAM dendrimers have substantially lower viscosity than polymers tested in Examples 6–8. Dendrimers (i.e., Gen 5) of much higher molecular weight than Mirapol A-15 have dramatically lower viscosity than Mirapol A-15.

EXAMPLES 11–15

Examples 1–10 were repeated with cationic polymers outside the scope of the invention. The results that were obtained are summarized in Table II.

TABLE II

| Example No. | Polymer | Weight Precipitate SLI/polymer | Corrected % Zein Solubilized |
|---|---|---|---|
| 11 | Jaguar 13-S | 0.053 | 42.8 ± 1.48 |
| 12 | Merquat 100 | 0.118 | 19.9 ± 4.90 |
| 13 | Merquat 550 | 0.0 | 39.9 ± 0.04 |
| 14 | Vege-Quat | 0.0 | 44.9 ± 0.01 |
| 15 | Control-SLI only | 0.0 | 50.2 ± 0.34 |

It can be seen from the comparison of results in Tables II and I that dendrimers lowered zein solubility to a significantly greater extent than cationic polymers of Examples 11, 13 and 14 which are outside the scope of the invention.

In Example 12 (also outside the scope of the invention), although Merquat 100 lowered zein solubility, it co-precipitated out substantially with an anionic surfactant.

EXAMPLES 16–25

Examples 1–10 were repeated except that a different surfactant was employed, i.e. 1% sodium dodecyl sulfate (SDS) was employed in place of SLI. The results that were obtained are summarized in Table III.

TABLE III

| Example No. | Polymer | Weight Precipitate SDS/polymer | Corrected % Zein Solubilized |
|---|---|---|---|
| 16 | Gen 0 | 0.002 | −1.8 ± 0.11 |
| 17 | Gen 1 | 0.0 | 34.8 ± 0.16 |
| 18 | Gen 2 | 0.0 | 35.4 ± 0.17 |
| 19 | Gen 3 | 0.0 | 31.2 ± 0.30 |
| 20 | Gen 5 | 0.0 | 31.5 ± 0.48 |
| 21 | Mirapol A-15 | 0.0 | 55.1 ± 0.50 |
| 22 | Polyvinylamine | 0.089 | 21.0 ± 0.89 |
| 23 | Polyethyleneimine | 0.258 | 6.8 ± 0.33 |
| 24 | Control - SDS only | 0.0 | 69.1 ± 0.72 |
| 25 | Water | 0.0 | 10.4 ± 0.56 |

It is important to note that in this case the control (Example 24) containing SDS exhibits a much higher level of zein solubilization than the control in Table I (Example 9), i.e., 69% versus 47%. This difference was expected since SDS is known to be a harsher surfactant than SLI. As can be seen from the results in Table III, dendrimers and polyvinylamine and polyethyleneimine lowered zein solubilization to a substantially greater extent than Mirapol A-15. Polyvinylamine, however, precipitated to a greater extent than dendrimers. Polyethyleneimine also formed a large precipitate.

EXAMPLES 26–32

Examples 1–10 were repeated except that 1% Ammonium Lauroyl Ethoxy Sulfate (ALES) was employed in place of SLI. The results that were obtained are summarized in Table IV.

TABLE IV

| Example No. | Polymer | Weight Precipitate ALES/polymer | Corrected % Zein Solubilized |
|---|---|---|---|
| 26 | Gen 0 | 0.0 | −10.5 ± 0.28 |
| 27 | Gen 1 | 0.0 | −4.1 ± 0.39 |
| 28 | Gen 5 | 0.175 | 7.8 ± 0.52 |
| 29 | Mirapol A-15 | 0.0 | 18.3 ± 0.21 |
| 30 | Polyvinylamine | 0.198 | 6.2 ± 1.01 |
| 31 | Polyethyleneimine | 0.339 | 9.6 ± 0.34 |
| 32 | Control-ALES only | 0.0 | 36.2 ± 0.02 |

As can be seen from Table IV, PAMAM dendrimers substantially lowered zein solubility compared to control and to Mirapol A-15. Polyvinylamine and polyethyleneamine also lowered zein solubility, but they co-precipitated out significantly with ALES.

EXAMPLE 33

The following shower gel composition was prepared:

| INGREDIENT | WEIGHT % |
|---|---|
| Mildness Aid | as in Table V |
| Ammonium Laureth Ethoxy Sulfate | 5 |
| Sodium Cocoyl Isethionate | 5 |
| Betaine | 10 |
| Castor Oil | 5 |
| Oleic Acid | 4.75 |
| $TiO_2$ | 0.5 |
| PEG 120-glucose dioleate | 0.5 |
| Water | to 100 |

Zein solubility was measured. The results that were obtained are summarized in Table V.

TABLE V

| POLYMER | WEIGHT % | % ZEIN SOLUBILIZED* |
|---|---|---|
| Gen 0 | 0.5 | 28 |
| Gen 1 | 0.5 | 35 |
| Gen 2 | 0.5 | 35 |
| Mirapol A-15 | 0.5 | 35 |
| Gen 0 | 1 | 18 |
| Gen 1 | 1 | 30 |
| Gen 2 | 1 | 32 |
| Mirapol A-15 | 1 | 28 |
| Gen 0 | 2 | −4 |
| Gen 1 | 2 | 8.9 |
| Gen 2 | 2 | 1.7 |
| Mirapol A-15 | 2 | 16 |
| Control (Shower gel without mildness aid) | — | 38 |

*All values have a mean deviation of 0.6.

Dendrimer generation 0 performed better than Mirapol A-15 at all concentrations. All dendrimers performed better than Mirapol A-15 at 2% concentration. It should also be noted again that dendrimers have substantially lower viscosity than Mirapol, are monodispersed and perform better than Mirapol in the presence of anionic surfactants harsher than SLI (i.e., SDS).

EXAMPLES 34–39

Effect of dendrimer concentration on zein solubility was investigated in the presence of 1% SLI at pH 7.1. The results that were obtained are summarized in Table VI.

TABLE VI

| Example No. | Dendrimer Type | Dendrimer Concentration | Weight Precipitate | Corrected % Zein Solubilized |
|---|---|---|---|---|
| 34 | Gen 2 | 0 | 0.00 | 63 ± 0.50 |
| 35 | | 0.1% | 0.01 | 49 ± 0.37 |
| 36 | | 0.2% | 0.02 | 31 ± 1.54 |
| 37 | Gen 5 | 0 | 0.00 | 63 ± 0.50 |
| 38 | | 0.1% | 0.00 | 53 ± 0.01 |
| 39 | | 0.2% | 0.00 | 39 ± 0.38 |

It can be seen from the results in Table VI, that at higher concentration of dendrimer, zein solubility is lower. The % zein solubilized is lower for Generation 2 Dendrimer than for Generation 5 dendrimer.

EXAMPLES 40–43

The effect of pH on zein solubility in the presence of a dendrimer (at 0.2%) and 1% SLI was investigated. The results that were obtained are summarized in Table VII.

TABLE VII

| Example # | 40 | 41 | 42 | 43 |
|---|---|---|---|---|
| pH | 10.5 | 8.6 | 7.1 | 5.4 |
| | % Zein Solubilized | | | |
| Gen 5 | 52.8 | 54.0 | 36.5 | 30.9 |
| Gen 3 | 48.4 | 50.7 | — | — |
| Gen 2 | 48.3 | 47.9 | 29.9 | 26.8 |
| Control-SLI only | 63.4 | 63.4 | 63.4 | 63.4 |

It is observed that the % zein solubilized by sodium lauroyl isethionate (SLI) decreases for the lower generation dendrimers at the various pH levels. The solution pH has an even stronger effect, and the % solubilization decreases to about 27% for Generation 2 at pH 5.4 relative to the control (about 63% at neutral pH). This decrease is significant, especially in relation to irritation potential. An exponential decrease in % zein solubilized takes place around pH 8, as the dendrimer amino group is being protonated. When a semi-log graph of the % zein solubilized versus the concentration of the protonated amine terminal group for a Generation 2 dendrimer (as calculated from the pH and assuming an average pKa of about 7.5 for the primary amine groups) is prepared, a linear relation is obtained with these dendrimers, and it is observed that it is the concentration of the protonated amine groups of the dendrimer, in equivalents per liter, that determines the zein solubility.

EXAMPLES 44–63

Zein solubility was tested in the presence of various dendrimers or cationic polymers and in the presence of cocoamidopropyl betaine (a zwitterionic surfactant). The results that were obtained are summarized in Table VIII.

TABLE VIII

| Example | Polymer | Polymer Conc. (%) | Initial pH | Final pH | % Sol. @ 48 hrs. | Avg. |
|---|---|---|---|---|---|---|
| 44 | Gen 0 | 0.2 | 9.76 | 5.74 | 11.35 | |
| 45 | | 0.2 | 9.74 | 5.74 | 11.40 | 11.38 ± .03 |
| 46 | Gen 1 | 0.2 | 9.51 | 5.74 | 10.82 | |
| 47 | | 0.2 | 9.51 | 5.74 | 10.82 | 10.82 ± 0 |
| 48 | Gen 2 | 0.2 | 9.24 | 5.77 | 10.94 | |
| 49 | | 0.2 | 9.24 | 5.74 | 10.77 | 10.85 ± 0.09 |
| 50 | Gen 3 | 0.2 | 9.34 | 5.79 | 10.58 | |
| 51 | | 0.2 | 9.31 | 5.76 | 10.57 | 10.57 ± 0.01 |
| 52 | Gen 5 | 0.2 | 9.36 | 5.78 | 11.08 | |
| 53 | | 0.2 | 9.35 | 5.79 | 10.82 | 10.95 ± 0.13 |
| 54 | Mirapol | 0.2 | 5.81 | 5.77 | 8.96 | |
| 55 | A-15 | 0.2 | 5.81 | 5.77 | 9.03 | 8.99 ± 0.04 |
| 56 | Polyvinyl- | 0.2 | 3.30 | 5.75 | 9.06 | |
| 57 | amine | 0.2 | 3.29 | 5.75 | 8.50 | 8.78 ± 0.28 |
| 58 | Polyeth- | 0.2 | 10.01 | 5.80 | 9.02 | |
| 59 | yleneimine | 0.2 | 10.01 | 5.81 | 9.41 | 9.22 ± 0.19 |
| 60 | Merquat | 0.2 | 5.66 | 5.81 | 8.73 | |
| 61 | 100 | 0.2 | 5.66 | 5.80 | 8.89 | 8.81 ± 0.08 |
| 62 | Control | 0 | 5.76 | 5.81 | 8.05 | |
| 63 | | 0 | 5.68 | 5.76 | 8.29 | 8.17 ± 0.12 |

No precipitate was observed in any of the examples. None of the polymers or dendrimers tested lowered zein solubility compared to control. This was expected because betaine is an amphoteric surfactant.

EXAMPLES 64–70

The effect of dendrimers on the critical micelle concentration (CMC) of the anionic surfactants (SLI and SDS) was investigated. The surface tension experiments were performed with a Lauda Tensiometer equipped with Model TE 1C controller and with SAE & KM3 computer (Brinkman Instruments, Westbury, N.Y.). The CMC of the surfactant was determined by adding a 0.1% dendrimer solution containing 10 mM surfactant to the reservoir of 0.1% dendrimer, in order to keep constant the concentration of the dendrimer. With sodium dodecyl sulfate, a 20 mM solution was prepared with the active polycation dendrimer. The CMC was taken at the break in the surface tension versus concentration plots. The results that were obtained are summarized in Table IX (pH in the range of 9–10).

TABLE IX

Effect of Dendrimers on CMC of Surfactants at pH 9–10

| Example No. | Dendrimer | Surfactant | CMC (mM/L) | C20 (mM/L) | CMC/C20 |
|---|---|---|---|---|---|
| 64 | None | SLI | 4.3 | 0.6 e–3 | 7.2 |
| 65 | Gen 2 | SLI | 0.40 | 0.8 e–3 | 5.0 |
| 66 | Gen 3 | SLI | 0.35 | 0.8 e–3 | 4.4 |
| 67 | Gen 5 | SLI | 0.20 | 0.6 e–3 | 3.3 |
| 68 | Gen 4.5 | SLI | 5.50 | 1.7 e–3 | 3.2 |
| 69 | None | SDS | 8.2 | | |
| 70 | Gen 3 | SDS | 0.33 | 0.12 e–3 | 2.8 |

Reduced CMC signifies reduced irritation potential. With SLI, generation 2, 3 and 5 dendrimers decreased the CMC by about ten fold. With SDS, the decrease was about twenty fold. The C20, which is the concentration of surfactant required to decrease the surface tension by 20 dynes/cm$^2$ is also given in Table IX, as well as the ratio of CMC/C20. The lower values of CMC/C20 suggest that micellization is preferred over adsorption in the presence of cationic dendrimers. This is also suggested by the effect of the half-generation (generation 4.5) carboxy-terminated dendrimer which raised the value of the CMC, i.e., the anionic dendrimer destabilized the surfactant micelles.

EXAMPLES 71–72

Typical soap bars according to the invention are as follows:

| Ingredient | #71 | #72 | min. | max. |
|---|---|---|---|---|
| Dendrimer | 5.0 | 2 | 0.5 | 40 |
| Sodium cocyl isethionate | 49.8 | 23.4 | 5 | 70 |
| Palmitic/Stearic acid | 20.2 | 5.7 | 1 | 50 |
| 82/18 soap (palmitic/stearic) | 8.3 | 49.3 | 5 | 95 |
| Sodium isethionate | 4.7 | 6 | .5 | 20 |
| Coconut Fatty acid | 3.1 | 2.4 | .5 | 20 |
| Sodium stearate | 3.0 | — | 2 | 20 |
| Alkyl benzene sulphonate | 2.0 | — | .1 | 10 |
| Perfume | 1.0 | 1.4 | 0.0 | 4 |
| Sodium chloride | 0.4 | 0.5 | .1 | 10 |
| Titanium dioxide | 0.2 | 0.8 | .01 | 4 |
| Water | 2.0 | 11.3 | .5 | 15 |
| Miscellaneous | 2.0 | .7 | .5 | 10 |
| Disodium phosphate | 5.0 | — | 0 | 1 |

EXAMPLES 73–76

Typical shower gel compositions according to the invention are as follows:

| Component | #73 | #74 | #75 | #76 | min. | max. |
|---|---|---|---|---|---|---|
| Dendrimer | 0.2 | 1 | 10 | 20 | 0.05 | 25 |
| Cocoamidopropyl Betaine | 8 | 2 | 10 | 8 | 0 | 20 |
| Ammonium laureth sulfate | 2 | 13 | 5 | 2 | 0 | 25 |
| Sodium cocoyl isethionate | 5 | | | 5 | 0 | 20 |
| Colorants | | | .0003 | | | |
| Dimethicone/laureth-4/-23 | 5 | | | 5 | 0 | 10 |
| Propylene glycol | 3 | | | | 0 | 10 |
| Glycerine | 1.3 | | | | 0 | 5 |
| Fragrance | 1.0 | 1–1.5 | | 0.6 | 0 | 4 |
| Carbomer | 10.2 | | | | 0 | 2 |
| DMDM Hydantoin | 0.2 | | | 0.2 | 0 | 3 |
| Sorbic Acid | | 0.4 | | | | |
| MICA/Titanium dioxide | 0.2 | | 0.5 | 0.2 | 0 | 4 |
| Guar gum (cationic) | 0.1 | | | 0.1 | 0 | 5 |
| Sodium hydroxide | 0.1 | | | | 0 | 2 |
| Sodium citrate | | 0.5 | | | 0 | 2 |
| BHT | 0.01 | | | .0075 | 0 | 1 |
| Water | to 100 | to 100 | | | to 100 | |
| Miscellaneous | 0–5 | ≈4 | | | 0 | 5 |
| Castor oil | — | 5 | | | 0 | 10 |
| Oleic acid | — | 5 | | | 0 | 10 |
| PEG 120 glucose dioleate | — | | 0.5 | | 0 | 5 |
| Sodium chloride or ammonium Sulfate | 1–3 | | (1.3) | | 0 | 5 |

The ingredients used in the Examples were obtained from the following suppliers:

| INGREDIENT | TRADENAME | SUPPLIER |
|---|---|---|
| Dendrimers | | Dendritech |
| Zein | | Eastman Kodak |
| Polyvinylamine | | National Starch Co. |
| Polyethyleneimine | | BASF |
| Polyquaternium 2 | Mirapol A-15 | Rhone-Poulenc |
| SLI | | Made in-house |
| Cationic Guar | E Jaquar 13-S | Rhone-Poulenc |
| Poly(DMDAAC) | F Merquat 100 | Calgon Corp. |
| Poly(DMDAAC) (Copolymer) | G Merquat 550 | Calgon Corp. |
| Cationic Protein | H Vege-Quat | Vege-Tech |
| Sodium dodecyl/sulfate | — | Spectrum/Lonza |
| Ammonium Laureth Sulfate | Standapol GA-Z | Henkel |
| Sodium Cocoyl Isethionate | Jordapon Cl-ADH | PPG-Mazer |
| Castor Oil | | Ashland Chem. |
| Oleic Acid | | Ashland Chem. |
| Cocoamidopropyl betaine | Tegobetaine F | Goldschmidt |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A mild personal cleansing composition comprising:
   (a) from about 0.05 to about 40 wt. % of a cationic dendrimer of generation n, where n is an integer from 0 to 10;
   (b) from about 1 to about 99% of an anionic surfactant; and (c) a cosmetically acceptable vehicle for the dendrimer and the anionic surfactant.

2. The composition of claim 1 wherein the dendrimer is selected from the group consisting of polyamidoamine dendrimers, polyethyleneimine dendrimers, polypropyleneimine dendrimers and mixtures thereof.

3. The composition of claim 1 wherein the composition is a liquid or a gel.

4. The composition of claim 3 wherein the dendrimer amount is in a range of from about 0.05 to about 25%.

5. The composition of claim 3 wherein the pH of the composition is no greater than 8.

6. The composition of claim 1 wherein the dendrimer is a polyamidoamine dendrimer.

7. The composition of claim 6 wherein n is an integer from 0 to 5.

8. The composition of claim 6 wherein n is an integer from 0 to 2.

9. The composition of claim 1 wherein the composition is a bar soap.

10. The composition of claim 9 wherein the dendrimer amount is in a range of from about 0.5 to about 40%.

11. A method of cleaning the skin while avoiding the harsh effects on the skin of an anionic surfactant by washing the skin with the composition according to claim 1.

* * * * *